(12) United States Patent  (10) Patent No.: US 7,566,713 B2
Mathews  (45) Date of Patent: Jul. 28, 2009

(54) IMMUNO INHIBITORY HETEROCYCLIC COMPOUNDS

(75) Inventor: Ian Richard Mathews, Abingdon (GB)

(73) Assignee: Medigene Limited (GB)

( * ) Notice: Subject to any disclaimer, the term of this patent is extended or adjusted under 35 U.S.C. 154(b) by 0 days.

(21) Appl. No.: 11/597,319

(22) PCT Filed: Apr. 26, 2005

(86) PCT No.: PCT/GB2005/001583

§ 371 (c)(1),
(2), (4) Date: Sep. 13, 2007

(87) PCT Pub. No.: WO2005/116033

PCT Pub. Date: Dec. 8, 2005

(65) Prior Publication Data

US 2008/0021033 A1 Jan. 24, 2008

(30) Foreign Application Priority Data

May 26, 2004 (GB) .................................. 0411770.1

(51) Int. Cl.
*A61K 31/4985* (2006.01)
*C07D 487/04* (2006.01)
*A61P 7/12* (2006.01)
(52) U.S. Cl. ........................ 514/248; 544/234; 544/115; 514/232.8
(58) Field of Classification Search .................. 514/248, 514/232.8; 544/234, 115
See application file for complete search history.

(56) References Cited

FOREIGN PATENT DOCUMENTS

WO WO 03/004495 A 1/2003
WO WO/2004/081011 * 9/2004
WO WO 2004/081011 A 9/2004

OTHER PUBLICATIONS

Huxley, et al., Chemistry & Biology, vol. 11, 1651-1658, Dec. 2004.*

* cited by examiner

*Primary Examiner*—Mark L Berch
*Assistant Examiner*—Cecilia M Jaisle
(74) *Attorney, Agent, or Firm*—Banner & Witcoff, Ltd.

(57) ABSTRACT

Compounds of formula (I) are CD80 inhibitors, and of value for immunomodulation, e.g. in rheumatoid arthritis, multiple sclerosis, diabetes, asthma, transplantation, systemic lupus erythematosis and psoriasis: wherein Y is —$CH_2$—, —$CH_2CH_2$—, or $CH_2CH_2CH_2$—; $R_1$ represents H; F; methyl, trifuoromethyl, methoxy or triflioromethoxy; $R_3$ represents H; F; Cl; Br; $NO_2$; CN; $C_1C_6$ alkyl optionally substituted by F or Cl; or $C_1$-$C_6$ alkoxy optionally substituted by F; $R_4$ represents a carboxylic acid group (—COOH) or an ester thereof, or —C(=O) $NR_6R_7$—$NR_7C$(=O)$R_6$, $NR_7C$(=O) $OR_6$, NHC(=O) or NHC(=S)$NR_7R_6$ wherein $R_6$ and $R_7$ are as defined in the specification and X represents a bond or a divalent radical as defined in the specification.

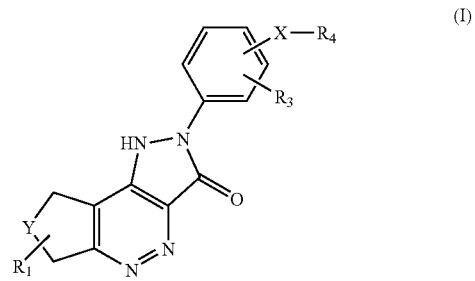

19 Claims, No Drawings

IMMUNO INHIBITORY HETEROCYCLIC COMPOUNDS

CROSS REFERENCE TO RELATED APPLICATIONS:

This application is a National Stage application of co-pending PCT application PCT/GB2005/001583 filed Apr. 26, 2005, which claims the benefit of Great Britain application number 0411770.1 filed May 26, 2004. These applications are incorporated herein by reference in their entireties.

The present invention relates to novel heterocyclic compounds, to methods for their preparation, to compositions containing them, and to methods and use for clinical treatment of medical conditions which may benefit from immunomodulation, e.g. rheumatoid arthritis, multiple sclerosis, diabetes, asthma, transplantation, systemic lupus erythematosis and psoriasis. More particularly the present invention relates to novel heterocyclic compounds, which are CD80 antagonists capable of inhibiting the interactions between CD80 and CD28.

BACKGROUND TO THE INVENTION

The immune system possesses the ability to control the homeostasis between the activation and inactivation of lymphocytes through various regulatory mechanisms during and after an immune response. Among these are mechanisms that specifically inhibit and/or turn off an immune response. Thus, when an antigen is presented by MHC molecules to the T-cell receptor, the T-cells become properly activated only in the presence of additional co-stimulatory signals. In the absence of these accessory signals there is no lymphocyte activation and either a state of functional inactivation termed anergy or tolerance is induced, or the T-cell is specifically deleted by apoptosis.

One such co-stimulatory signal involves interaction of CD80 on specialised antigen-presenting cells with CD28 on T-cells, and this signal has been demonstrated to be essential for full T-cell activation. (Lenschow et al. (1996) *Annu. Rev. Immunol.*, 14, 233-258). It would therefore be desirable to provide compounds which inhibit this CD80/CD28 interaction.

DETAILED DESCRIPTION OF THE INVENTION

According to the present invention there is provided a compound of formula (I) or a pharmaceutically or veterinarily acceptable salt, hydrate or solvate thereof:

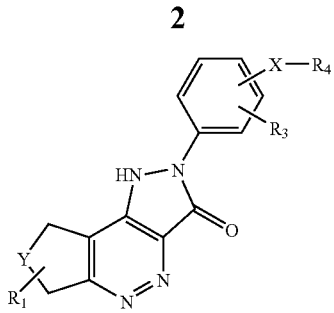

wherein
Y is $-CH_2-$, $-CH_2CH_2-$, or $-CH_2CH_2CH_2-$;
$R_1$ represents H; F; methyl, trifuoromethyl, methoxy or triflioromethoxy;
$R_3$ represents H; F; Cl; Br; $-NO_2$; $-CN$; $C_1-C_6$ alkyl optionally substituted by F or Cl; or $C_1-C_6$ alkoxy optionally substituted by F;
$R_4$ represents a carboxylic acid group ($-COOH$) or an ester thereof, or $-C(=O)NR_6R_7$, $-NR_7C(=O)R_6$, $-NR_7C(=O)OR_6$, $-NHC(=O)NR_7R_6$ or $-NHC(=S)NR_7R_6$ wherein
$R_6$ represents H, or a radical of formula -(Alk)$_m$-Q wherein
m is 0 or 1
Alk is an optionally substituted divalent straight or branched $C_1-C_{12}$ alkylene, or $C_2-C_{12}$ alkenylene, or $C_2-C_{12}$ alkynylene radical or a divalent $C_3-C_{12}$ carbocyclic radical, any of which radicals may be interrupted by one or more $-O-$, $-S-$ or $-N(R_8)-$ radicals wherein $R_8$ represents H or $C_1-C_4$ alkyl, $C_3-C_4$ alkenyl, $C_3-C_4$ alkynyl, or $C_3-C_6$ cycloalkyl, and
Q represents H; $-NR_8R_8$ wherein each $R_8$ independently represents H; $C_1-C_4$ alkyl; $C_3-C_4$ alkenyl; $C_3-C_4$ alkynyl; $C_3-C_6$ cycloalkyl; an ester group; an optionally substituted carbocyclic or heterocyclic group; or form a ring when taken together with the nitrogen to which they are attached, which ring is optionally substituted; and
$R_7$ represents H or $C_1-C_6$ alkyl; or when taken together with the atom or atoms to which they are attached $R_6$ and $R_7$ form an optionally substituted monocyclic heterocyclic ring having 5, 6 or 7 ring atoms; and
X represents a bond or a divalent radical of formula -(Z)$_n$-(Alk)- or -(Alk)-(Z)$_n$- wherein Z represents $-O-$, $-S-$ or $-NH-$, Alk is as defined in relation to $R_6$ and n is 0 or 1.

Compounds (I) may exist in the form of tautomers ($I^1$) and ($I^2$):

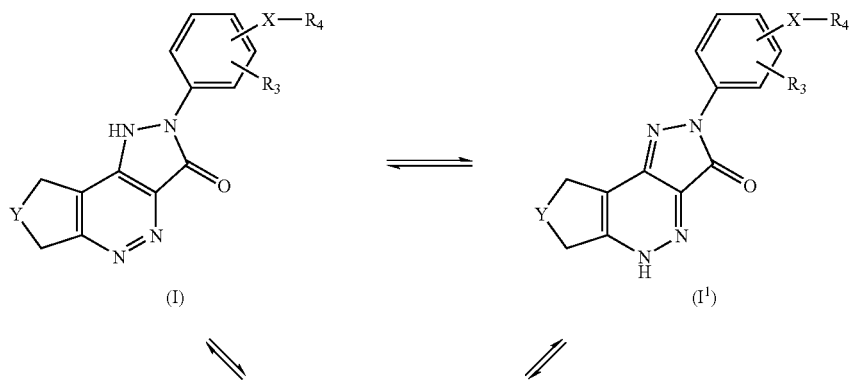

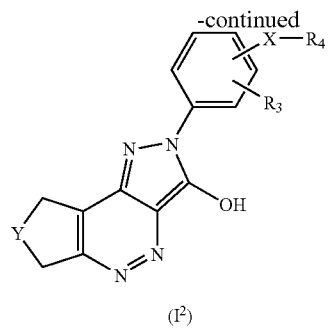

(I²)

Hereafter, the compounds of the invention may be represented and referred to in either tautomeric form (I), and it is to be understood that any and all tautomeric forms of structure (I), in particular (I¹) and (I²), are included in the invention.

Compounds of general formula (I) are CD80 antagonists. They inhibit the interaction between CD80 and CD28 and thus the activation of T cells, thereby modulating the immune response.

Accordingly the invention also includes:
(i) a compound of formula (I) or a pharmaceutically or veterinarily acceptable salt thereof for use in the treatment of conditions which benefit from immunomodulation.
(ii) the use of a compound of formula (I) or a pharmaceutically or veterinarily acceptable salt thereof in the manufacture of a medicament for the treatment of conditions which benefit from immunomodulation.
(iii) a method of immunomodulation in mammals, including humans, comprising administration to a mammal in need of such treatment an immunomodulatory effective dose of a compound of formula (I) or a pharmaceutically or veterinarily acceptable salt thereof.
(iv) a pharmaceutical or veterinary composition comprising a compound of formula (I) or a pharmaceutically or veterinarily acceptable salt thereof together with a pharmaceutically or veterinarily acceptable excipient or carrier.

Conditions which benefit from immunomodulation include:
Acute disseminated encephalomyelitis
Adrenal insufficiency
Allergic angiitis and granulomatosis
Amylodosis
Ankylosing spondylitis
Asthma
Autoimmune Addison's disease
Autoimmune alopecia
Autoimmune chronic active hepatitis
Autoimmune haemolytic anaemia
Autoimmune thrombocytopenic purpura
Behcet's disease
Cerebellar degeneration
Chronic active hepatitis
Chronic inflammatory demyelinating polyradiculoneuropathy
Chronic neuropathy with monoclonal gammopathy
Classic polyarteritis nodosa
Congenital adrenal hyperplasia
Cryopathies
Dermatitis herpetiformis
Diabetes
Eaton-Lambert myasthenic syndrome
Encephalomyelitis
Epidermolysis bullosa acquisita
Erythema nodosa
Gluten-sensitive enteropathy
Goodpasture's syndrome
Guillain-Barre syndrome
Hashimoto's thyroiditis
Hyperthyroidism
Idiopathic hemachromatosis
Idiopathic membranous glomerulonephritis
Isolated vasculitis of the central nervous system
Kawasaki's disease
Minimal change renal disease
Miscellaneous vasculitides
Mixed connective tissue disease
Multifocal motor neuropathy with conduction block
Multiple sclerosis
Myasthenia gravis
Opsoclonus-myoclonus syndrome
Pemphigoid
Pemphigus
pernicious anaemia
Polymyositis/dermatomyositis
Post-infective arthritides
Primary biliary sclerosis
Psoriasis
Reactive arthritides
Reiter's disease
Retinopathy
Rheumatoid arthritis
Sclerosing cholangitis
Sjögren's syndrome
Stiff-man syndrome
Subacute thyroiditis
Systemic lupus erythematosis
Systemic necrotizing vasculitides
Systemic sclerosis (scleroderma)
Takayasu's arteritis
Temporal arteritis
Thromboanglitis obliterans
Type I and type II autoimmune polyglandular syndrome
Ulcerative colitis
Uveitis
Wegener's granulomatosis As used herein, the term "ester" refers to a group of the form —COOR, wherein R is a radical notionally derived from the alcohol ROH. Examples of ester groups include the physiologically hydrolysable esters such as the methyl, ethyl, n- and iso-propyl, n-, sec- and tert-butyl, and benzyl esters.

As used herein the term "alkylene" refers to a straight or branched alkyl chain having two unsatisfied valencies, for example —CH$_2$—, —CH$_2$CH$_2$—, —CH$_2$CH$_2$CH$_2$—, —CH(CH$_3$)CH$_2$—, —CH(CH$_2$CH$_3$)CH$_2$CH$_2$CH$_2$—, and —C(CH$_3$)$_3$.

As used herein the term "alkenylene" refers to a straight or branched alkenyl chain having two unsatisfied valencies, for example —CH═CH—, —CH$_2$CH═CH—, —C(CH$_3$)═CH—, and —CH(CH$_2$CH$_3$)CH═CHCH$_2$—.

As used herein the term "alkynylene" refers to a straight or branched alkynyl chain having two unsatisfied valencies, for example —C≡C—, —CH$_2$C≡C—, and —CH(CH$_2$CH$_3$)C≡CCH$_2$—.

Unless otherwise specified in the context in which it occurs, the term "substituted" as applied to any moiety herein means substituted with at least one substituent, selected from, for example, (C$_1$-C$_6$)alkyl, (C$_1$-C$_6$)alkenyl, (C$_2$-C$_6$)alkynyl, fluoro-substituted(C$_1$-C$_6$)alkyl, fluoro-substituted(C$_1$-C$_6$)alkenyl, fluoro-substituted(C$_2$-C$_6$)alkynyl, (C$_1$-C$_6$)alkoxy and fluoro-substituted(C$_1$-C$_6$)alkoxy (including the special case where a ring is substituted on adjacent ring C atoms by alkylenedioxy such as methylenedioxy or ethylenedioxy), (C$_1$-C$_6$)alkylthio, phenyl, benzyl, phenoxy, benzyloxy, hydroxy, mercapto, amino, fluoro, chloro, bromo, cyano, nitro, oxo, —COOH, —SO$_2$OH, —CONH$_2$, —SO$_2$NH$_2$, —COR$^A$, —COOR$^A$, —SO$_2$OR$^A$, —NHCOR$^A$, —NHSO$_2$R$^A$, —CONHR$^A$, —SO$_2$NHR$^A$, —NHR$^A$, —NR$^A$R$^B$, —CONR$^A$R$^B$ or —SO$_2$NR$^A$R$^B$ wherein R$^A$ and R$^B$ are independently a (C$_1$-C$_6$)alkyl or (C$_2$-C$_6$)alkoxy group or a monocyclic carbocyclic or heterocyclic group of from 5-7 ring members, or R$^A$ and R$^B$ form a ring when taken together with the nitrogen to which they are attached. In the case where "substituted" means substituted by phenyl, benzyl, phenoxy, or benzyloxy, the phenyl ring thereof may itself be substituted with any of the foregoing, except phenyl, benzyl, phenoxy, or benzyloxy.

As used herein the term "aryl" refers to a mono-, bi- or tri-cyclic carbocyclic aromatic radical, and to two such radicals covalently linked to each other, Illustrative of such radicals are phenyl, biphenyl and napthyl.

As used herein the unqualified term "carbocyclyl" or "carbocyclic" includes aryl, cycloalkyl and cycloalkenyl and refers to a ring system (monocyclic, bicyclic, tricyclic or bridged) whose ring atoms are all carbon.

As used herein the unqualified term "cycloalkyl" refers to a carbocyclic ring system which contains only single bonds between ring carbons.

As used herein the unqualified term "cycloalkenyl" refers to a carbocyclic ring system which contains at least one double bond between a pair of ring carbons.

As used herein the term "heteroaryl" refers to a mono-, bi- or tri-cyclic aromatic radical containing one or more heteroatoms selected from S, N and O. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in particular means a mono-, bi- or tri-cyclic or bridged non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, tetrahydrofuranyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, tetrahydropyranyl, quinuclidinyl, isoxazolyl, benzimidazolyl, methylenedioxyphenyl, ethylenedioxyphenyl, maleimido and succinimido groups.

Some compounds of the invention contain one or more chiral centres because of the presence of asymmetric carbon atoms. The presence of asymmetric carbon atoms gives rise to stereoisomers or diastereoisomers with R or S stereochemistry at each chiral centre. The invention includes all such stereoisomers and diastereoisomers and mixtures thereof.

As used herein the term "salt" includes base addition, acid addition and quaternary salts. Compounds of the invention which are acidic can form salts, including pharmaceutically or veterinarily acceptable salts, with bases such as alkali metal hydroxides, e.g. sodium and potassium hydroxides; alkaline earth metal hydroxides e.g. calcium, barium and magnesium hydroxides; with organic bases e.g. N-ethyl piperidine, dibenzylamine, choline, and the like. Those compounds (I) which are basic can form salts, including pharmaceutically or veterinarily acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic and p-toluene sulphonic acids and the like.

Methods

Compounds of the invention wherein R$_4$ represents an amide group —C(═O)NR$_6$R$_7$ may be prepared by reaction of the appropriate amine HNR$_6$R$_7$ with a compound of formula (II) to amidate the carboxylic acid group:

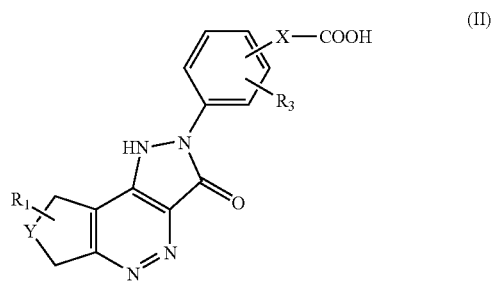

(II)

the symbols R$_1$, R$_3$, X, R$_6$ and R$_7$ being as defined in relation to formula (I) above.

Compounds (II) (ie compounds (I) of the invention wherein R$_4$ is a carboxylic acid group) may be prepared by reaction of a compound of formula (III) with a hydrazine of formula (IV):

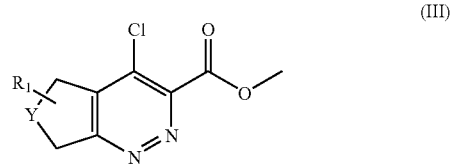

(III)

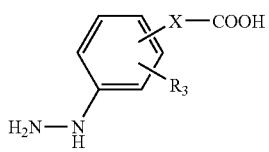

(IV)

This reaction may result in the preparation of a mixture of the position isomers (IIA) and (IIB):

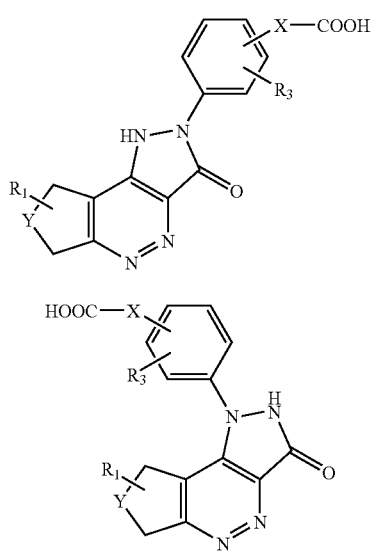

from which the desired isomer (IIA) may be separated.

Compounds (III) may be prepared as described in International Patent Application WO 99/00391.

Compounds (I) wherein $R_4$ is an ester or amide group may also be prepared from intermediate (III) by reaction with the appropriate hydrazine (IVA)

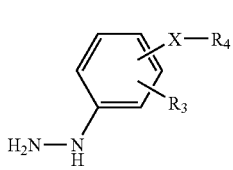

(IVA)

wherein $R_4$ is an ester or amide group. Again the reaction may result in a mixture of the ester or amide analogues of the carboxylic acids (IIA) and (IIB), from which the desired ester or amide isomer (I) may be separated. Alternatively, the carboxylic acid compound (II) may simply be esterified, or amidated.

Compounds (I) wherein $R_4$ is a "reverse amide" group —$NR_7C(=O)R_6$ may be prepared by Curtius rearrangement (see Ninomiya, K.; Shioiri, T.; Yamada, S. Tetrahedron (1974), 30(14), 2151-7) of the carboxylic acid (II) to the isocyanate (V)

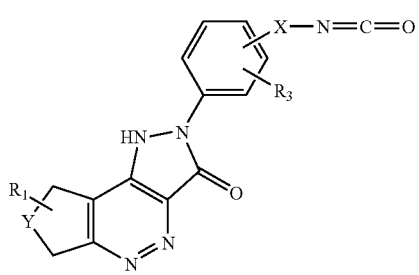

(V)

followed by hydrolysis of the isocyanate group to an amino group and acylation of the amino group with, for example, the acid chloride Cl—C(=O)$R_6$. In cases where $R_7$ is not hydrogen, the $R_7$ substituent may be introduced after the isocyanate reduction step or after the acylation step.

In an alternative route to the "reverse amide" ($R_4 = $ —$NR_7C(=O)R_6$) compounds of the invention, a compound of structure (V) in which the isocyanate moiety is replaced by a nitro group may be reduced to the corresponding amine, which may then be acylated to form the desired reverse amide.

Compounds (I) wherein $R_4$ is a urea group —NHC(=O) $NHR_6$ or thiourea group —NHC(=S)$NHR_6$ may also be prepared from the isocyanate (V) or the corresponding isothiocyanate by reaction with the appropriate amine $H_2NR_6$.

Compounds (I) wherein $R_4$ is a carbamate group —$NR_7C$ (=O)$OR_6$ may be prepared by the reaction of the isocyanate with an appropriate alcohol $R_6OH$.

Further details of the synthetic methods for the preparation of compounds (I) of the invention, and intermediates such as (III), may be found in the examples herein.

In the compounds of the invention:

Y is —$CH_2$—, —$CH_2CH_2$—, or —$CH_2CH_2CH_2$, so that the ring of which Y is a part is a benz-fused 5-, 6- or 7-membered ring. Currently it is preferred that Y be —$CH_2CH_2$—.

The radical $R_4X$— is preferably in the 4-position of the phenyl ring.

X may be, for example a bond, or a —$CH_2$— or —$CH_2CH_2$' radical. A bond is presently preferred.

$R_3$ may be, for example, H, F, Cl, methyl, methoxy, or methylenedioxy. Currently it is preferred that $R_3$ is H.

$R_1$ may be, for example, H, F, Cl, methyl, methoxy. Currently it is preferred that $R_1$ be hydrogen or fluoro.

$R_4$ represents a carboxylic acid group (—COOH) or an ester thereof, or —C(=O)$NR_6R_7$, —$NR_7C(=O)R_6$, —$NR_7C(=O)OR_6$ or —NHC(=O)$NHR_6$, all as defined above.

When $R_4$ is an ester group, examples include those of formula —COOR wherein R is methyl, ethyl n- or isopropyl, n-, sec- or tert-butyl, or benzyl ester.

$R_6$, when present, represents H, or a radical of formula -(Alk)$_m$-Q wherein m, Alk and Q being as defined above. When m is 1, Alk may be, for example a straight or branched $C_1$-$C_6$ alkylene radical, such as —$CH_2$—, —$CH_2CH_2$—, —$CH_2CH_2CH_2$—, and —$CH_2CH(CH_3)$ $CH_2$—. Alk may also be, for example, a divalent cyclopropylene, cyclopentylene or cyclohexylene radical. The radical Alk may be optionally substituted by, for example, OH, oxo, $CF_3$, methoxy or ethoxy. The radical Alk may optionally contain a hetero atom, for example in the form of an ether, thioether or amino linkage.

The group Q may represent, for example, hydrogen; —$NR_8R_8$ wherein each $R_8$ may be the same or different and selected from hydrogen, methyl, ethyl, n- or isopropyl or tert-butyl; an ester group for example a methyl, ethyl or benzyl ester; or an optionally substituted aryl, aryloxy, cycloalkyl, cycloalkenyl or heterocyclic group, for example phenyl, phenoxy, cyclopentyl, cyclohexyl, furyl, thienyl, piperidyl, or piperazinyl group.

$R_7$ when present represents H or $C_1$-$C_6$ alkyl, for example methyl, ethyl n- or iso-propyl, n-, sec- or tert-butyl; or when taken together with the atom or atoms to which they are attached $R_6$ and $R_7$ form a monocyclic heterocyclic ring having 5, 6 or 7 ring atoms.

Especially preferred are the cases where $R_4$ represents —C(=O)$NR_6R_7$ or —NHC(=O)$NR_7R_6$ wherein $R_7$ is hydrogen and $R_6$ represents a radical of formula -(Alk)$_m$-Q wherein m is 1 and the divalent radical Alk contains 3 or 4 carbon atoms and is unsubstituted, and Q represents —$NR_8R_8$ wherein each $R_8$ independently represents H; $C_1$-$C_4$ alkyl; $C_3$-$C_4$ alkenyl; $C_3$-$C_4$ alkynyl; $C_3$-$C_6$ cycloalkyl; an ester group; an optionally substituted carbocyclic or heterocyclic group; or form a ring when taken together with the nitrogen to which they are attached, which ring is optionally substituted. In such cases a particular example of Q is the quinuclidine radical.

A specific preferred subset of compounds of the invention has formula (IC):

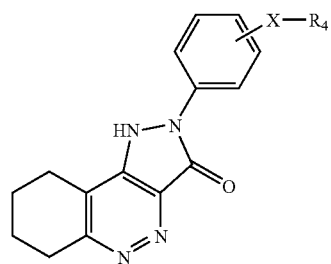

(IC)

wherein X and $R_4$ are as specified above. In this subset, the radical $R_4$X— may be in the 4-position of the phenyl ring. This subset includes in particular, compounds wherein X is a bond and $R_4$ is —C(=O)$NR_6R_7$ wherein $R_6$ and $R_7$ are as specified above.

Specific compounds of the invention include those of the Examples herein.

As mentioned above, the invention includes pharmaceutical or veterinary composition comprising a compound of formula (I) or a pharmaceutically or veterinarily acceptable salt thereof together with a pharmaceutically or veterinarily acceptable excipient or carrier. In such compositions, it will be understood that the specific dose level for any particular patient will depend upon a variety of factors including the activity of the specific compound employed, the age, body weight, general health, sex, diet, time of administration, route of administration, rate of excretion, drug combination and the cause and severity of the particular disease undergoing therapy. Optimum dose levels and frequency of dosing will be determined by clinical trial.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Embodiments of the invention are described in the following non-limiting Examples:

The following abbreviations are used in the experimental descriptions:

| | |
|---|---|
| DMF | Dimethyl formamide |
| DMA | Dimethyl acetamide |
| DMSO | Dimethyl sulphoxide |
| HBTU | O-Benzotriazol-1-yl-N,N,N',N'-tetramethyluronium hexafluorophosphate |
| HPLC | High performance liquid chromatography |
| LCMS | Liquid chromatography mass spectrum |
| NMR | Nuclear magnetic resonance spectroscopy |

EXAMPLE 1

Preparation of 4-(3-Oxo-1,3,5a,6,7,8,9,9a-octahydro-pyrazolo[4,3-c]cinnolin-2-yl)-benzoic acid

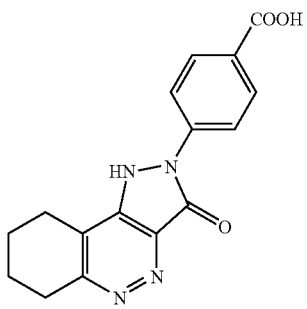

4-(3-Oxo-1,3-dihydro-pyrazolo[4,3-c]cinnolin-2-yl)-benzoic acid (1.70 g) was dissolved in trifluoroacetic acid (20 ml) in a glass lined hydrogenation bomb. Catalyst ($PtO_2$, 170 mg) was added under inert atmosphere. The hydrogenation bomb was sealed, purged with nitrogen and pressurised to 6-7 bar with hydrogen gas. The mixture was stirred at 25° C. overnight.

The mixture was diluted with water (20 ml) and the catalyst was removed by filtration through a glass fibre filter. The filtrate was basified with saturated sodium carbonate solution to pH 8-9 to give a brown solution. The aqueous phase was washed with ethyl acetate (2×100 ml) and then acidified to pH 3-4 with 1 M HCl to give a dark red solution. The aqueous phase was again washed with ethyl acetate (1×100 ml). Then extracted with n-butanol (3×100 ml). The combined organic phase was concentrated under vacuum until a dark red oil remained. The oil was diluted with ethyl acetate and precipitation of a dark red solid was observed. The solids were collected by filtration and dried under vacuum.

LC-MS isolated solid; main peak [M+H]+311 of required product. Yield: 535 mg, 27% (uncorrected for impurities and residual solvents).

EXAMPLE 2

Preparation of N-(3-Dimethylamino-propyl)-4-(3-oxo-1,3,6,7,8,9-hexahydro-pyrazolo[4,3-c]cinnolin-2-yl)-benzamide

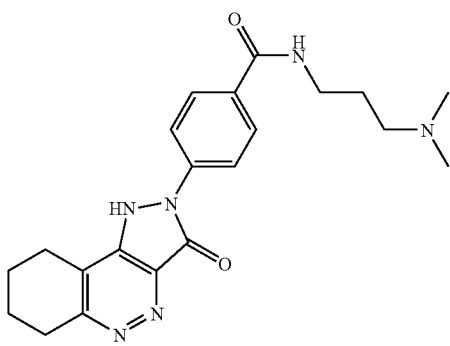

4-(3-Oxo-1,3,5a,6,7,8,9,ga-octahydro-pyrazolo[4,3-c]cinnolin-2-yl)-benzoic acid was weighed into a vial (100 mg).

Anhydrous DMA (1 ml) and dry Hunig's base (144 mg, 0.195 ml) were added followed by HBTU (106 mg). A dark brown suspension was obtained and stirred at room temperature for 10 minutes. N',N'-Dimethyl-propane-1,3-diamine (0.28 mmol) was added and the mixture stirred overnight at room temperature. Purification yielded the desired product (MH+= 395).

The compounds of Examples 3 to 6 below were prepared analogously:

EXAMPLE 3

N-(2,2-Difluoro-ethyl)-4-(3-oxo-1,3,6,7,8,9-hexahydro-pyrazolo[4,3-c]cinnolin-2-yl)-benzamide

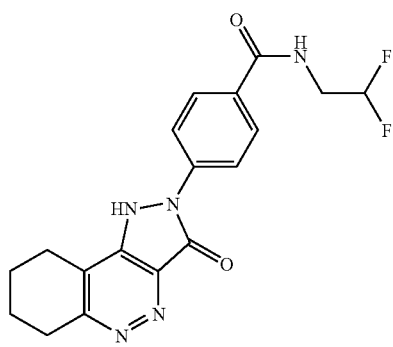

MS: MH=421.2

EXAMPLE 4

N-(3-Cyclohexylamino-propyl)-4-(3-oxo-1,3,6,7,8,9-hexahydro-pyrazolo[4,3-c]cinnolin-2-yl)-benzamide

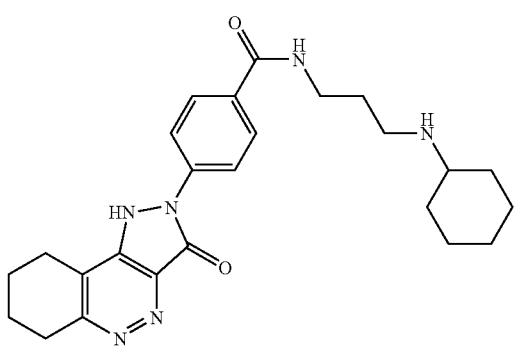

MS: MH+449.2

EXAMPLE 5

4-(3-Oxo-1,3,6,7,8,9-hexahydro-pyrazolo[4,3-c]cinnolin-2-yl)-N-(4-pyrrolidin-1-yl-butyl)-benzamide

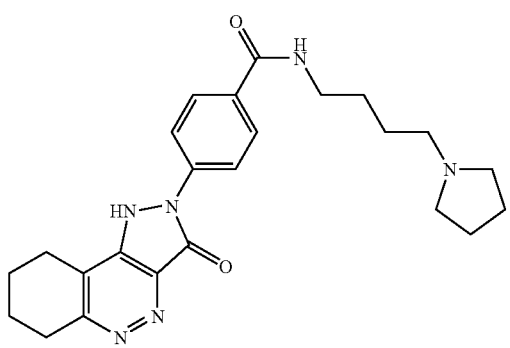

MS: MH+435.2

EXAMPLE 6

4-(3-Oxo-1,3,6,7,8,9-hexahydro-pyrazolo[4,3-c]cinnolin-2-yl)-N-(1,2,2,6,6-pentamethyl-piperidin-4-yl)-benzamide

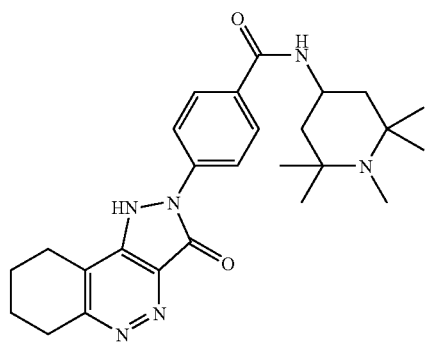

MS: MH+463.2

Time Resolved Fluorescence Assay

The examples described above were tested in a cell free Homogenous Time Resolved Fluorescence (TRFret) assay to determine their activity as inhibitors of the CD80-CD28 interaction.

In the assay, europium and allophycocyanin (APC) are associated with CD28 and CD80 indirectly (through antibody linkers) to form a complex, which brings the europium and APC into close proximity to generate a signal. The complex comprises the following six proteins: fluorescent label 1, linker antibody 1, CD28 fusion protein, CD80 fusion protein, linker antibody 2, and fluorescent label 2. The table below describes these reagents in greater detail.

| | |
|---|---|
| Fluorescent label 1 | Anti-Rabbit IgG labelled with Europium (1 µg/ml) |
| Linker antibody 1 | Rabbit IgG specific for mouse Fc fragment (3 µg/ml) |
| CD28 fusion protein | CD28 - mouse Fc fragment fusion protein (0.48 µg/ml) |
| CD80 fusion protein | CD80 mouse Fab fragment (C215) fusion protein (1.9 µg/ml) |
| Linker antibody 2 | GαMκ-biotin: biotinylated goat IgG specific for mouse kappa chain (2 µg/ml) |
| Fluorescent label 2 | SA-APC: streptavidin labelled allophycocyanin (8 µg/ml) |

On formation of the complex, europium and APC are brought into proximity and a signal is generated.

Non-specific interaction was measured by substituting a mouse Fab fragment (C215) for the CD80 mouse Fab fragment fusion protein (1.9 µg/ml). The assay was carried out in black 384 well plates in a final volume of 30 µl. Assay buffer: 50 mM Tris-HCl, 150 mM NaCl pH7.8, containing 0.1% BSA (w/v) added just prior to use.

Compounds were added to the above reagents in a concentration series ranging between 100 µM-1.7 nM. The reaction was incubated for 4 hours at room temperature. Dual measurements were made using a Wallac Victor 1420 Multilabel Counter. First measurement: excitation 340 nm, emission 665 nm, delay 50 µs, window time 200 µs. second measurement: excitation 340 nm, emission 615 nm, delay 50 µs, window time 200 µs. Counts were automatically corrected for fluorescence crossover, quenching and background.

The compounds of Examples 1- 8 had the following activities in the HTRF assay described above:

| Example No. | Activity (EC50) |
|---|---|
| 1 | >10 µM |
| 2 | 63 nm |
| 3 | 790 nm |
| 4 | 101 nm |
| 5 | 60 nm |
| 6 | 93 nm |

The invention claimed is:

1. A compound of formula (I) or a pharmaceutically or veterinarily acceptable salt thereof:

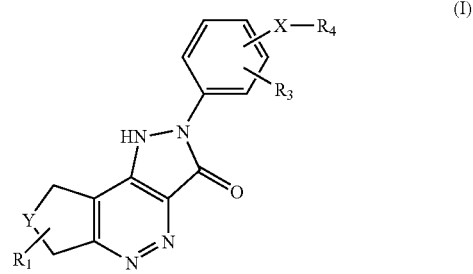

wherein

Y is —$CH_2$—, —$CH_2CH_2$—, or —$CH_2CH_2CH_2$—;

$R_1$ represents H; F; methyl, trifluoromethyl, methoxy or trifluoromethoxy;

$R_3$ represents H; F; Cl; Br; —$NO_2$; —CN; $C_1$-$C_6$ alkyl optionally substituted by F or Cl; or $C_1$-$C_6$ alkoxy optionally substituted by F;

R₄ represents a carboxylic acid group (—COOH) or an ester group of formula COOR wherein R is methyl, ethyl, n- or iso-propyl, n-, sec-, or tert-butyl or benzyl, or —C(=O)NR₆R₇, —NR₇C(=O)R₆, —NR₇C(=O)OR₆, —NHC(=O)NR₇R₆ or —NHC(=S)NR₇R₆ wherein R₆ represents H, or a radical of formula -(Alk)$_m$-Q wherein
m is 0 or 1
Alk is an optionally substituted divalent straight or branched $C_1$-$C_{12}$ alkylene, or $C_2$-$C_{12}$ alkenylene, or $C_2$-$C_{12}$ alkynylene radical or a divalent $C_3$-$C_{12}$ carbocyclic radical, any of which radicals may be interrupted by one or more —O—, —S— or —N(R₈)- radicals wherein R₈ represents H or $C_1$-$C_4$ alkyl, $C_3$-$C_4$ alkenyl, $C_3$-$C_4$ alkynyl, or $C_3$-$C_6$ cycloalkyl, and
Q represents H; —NR₈R₈ wherein each R₈ independently represents H; $C_1$-$C_4$ alkyl; $C_3$-$C_4$ alkenyl; $C_3$-$C_4$ alkynyl; $C_3$-$C_6$ cycloalkyl; an ester group of formula COOR wherein R is methyl, ethyl, n- or iso-propyl, n-, sec-, or tert-butyl or benzyl; an optionally substituted carbocyclic or heterocyclic group; or form a ring when taken together with the nitrogen to which they are attached, which ring is optionally substituted; and
R₇ represents H or $C_1$-$C_6$ alkyl; or when taken together with the atom or atoms to which they are attached R₆ and R₇ form an optionally substituted monocyclic heterocyclic ring having 5, 6 or 7 ring atoms; and
X represents a bond or a divalent radical of formula -(Z)$_n$-(Alk)- or -(Alk)-(Z)$_n$- wherein Z represents —O—, —S— or —NH—, Alk is as defined in relation to R₆ and n is 0 or 1.

2. A compound as claimed in claim 1 wherein Y is —CH₂CH₂—.

3. A compound as claimed in claim 1 wherein the radical R₄X— is in the 4-position of the phenyl ring.

4. A compound as claimed in claim 1 wherein X is a bond.

5. A compound as claimed in claim 1 wherein R₃ is hydrogen.

6. A compound as claimed in claim 1 wherein R₁ is hydrogen or fluoro.

7. A compound as claimed in claim 1 wherein R₄ represents —C(=O)NR₆R₇.

8. A compound as claimed in claim 1 wherein R₄ represents —NHC(=O)NR₇R₆.

9. A compound as claimed in claim 1 wherein R₆ represents a radical of formula -(Alk)$_m$-Q wherein m is 1 and the divalent radical Alk contains 3 or 4 carbon atoms and is unsubstituted, and Q represents —NR₈R₈ wherein each R₈ independently represents H; $C_1$-$C_4$ alkyl; $C_3$-$C_4$ alkenyl; $C_3$-$C_4$ alkynyl; $C_3$-$C_6$ cycloalkyl; an ester group of formula COOR wherein R is methyl, ethyl, n- or iso-propyl, n-, sec-, or tert-butyl of benzyl; an optionally substituted carbocyclic or heterocyclic group; or form a ring when taken together with the nitrogen to which they are attached, which ring is optionally substituted.

10. A compound as claimed in claim 9 wherein Q is a quinuclidine radical.

11. A compound as claimed in claim 7 wherein R₇ is hydrogen.

12. A compound as claimed in claim 1 wherein R₆ represents a radical of formula -(Alk)$_m$-Q wherein m is 1, Alk is —CH₂—, —CH₂CH₂, —CH₂CH₂CH₂—, or —CH₂CH(CH₃)CH₂—, or a divalent cyclopropylene, cyclopentylene or cyclohexylene radical, optionally substituted by OH, oxo, CF₃, methoxy or ethoxy, and Q represents hydrogen; —NR₈R₈ wherein each R₈ may be the same or different and selected from hydrogen, methyl, ethyl, n- or isopropyl or tert-butyl; a methyl, ethyl or benzyl ester; or an optionally substituted phenyl, phenoxy, cyclopentyl, cyclohexyl, furyl, thienyl, piperidyl, or piperazinyl group.

13. A compound as claimed in claim 1 wherein R₇ represents methyl, ethyl, n- or iso-propyl, n-, sec- or tert-butyl; or when taken together with the atom or atoms to which they are attached R₆ and R₇ form a monocyclic heterocyclic ring having 5, 6 or 7 ring atoms.

14. A compound as claimed in claim 1 wherein R₁ is F, in the 6-position of the 3-oxo-1,3-dihydro-2H-pyrazolo[4,3-c]cinnolin-2-yl ring system.

15. A compound as claimed in claim 1 wherein X is a bond, or a —CH₂— or —CH₂CH₂— radical.

16. A compound of formula (IC) or a pharmaceutically or veterinarily acceptable salt thereof:

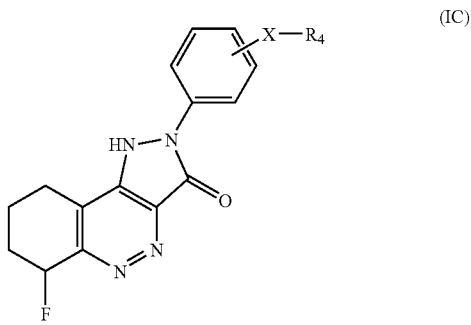

(IC)

wherein X is a bond, or a —CH₂— or —CH₂CH₂— radical and R₄ represents a carboxylic acid group (—COOH) or an ester group of formula COOR wherein R is methyl, ethyl, n- or iso-propyl, n-, sec- or tert-butyl or benzyl, or —C(=O)NR₆R₇, —NR₇C(=O)R₆, —NR₇C(=O)OR₆, —NHC(=O)NR₇R₆or
—NHC(=S)NR₇R₆ wherein
R₆ represents a radical of formula -(Alk)$_m$-Q wherein m is 1 and
the divalent radical Alk contains 3 or 4 carbon atoms and is unsubstituted, and Q represents —NR₈R₈ wherein each R₈ independently represents H; $C_1$-$C_4$ alkyl; $C_1$-$C_4$ alkenyl, $C_3$-$C_4$ alkynyl; $C_3$-$C_6$ cycloalkyl; an ester group; an optionally substituted carbocyclic or heterocyclic group; or form a ring when taken together with the nitrogen to which they are attached, which ring is optionally substituted; or
Alk is —CH₂—, —CH₂CH₂, —CH₂CH₂CH₂—, or —CH₂CH(CH₃)CH₂—, or a divalent cyclopropylene, cyclopentylene or cyclohexylene radical, optionally substituted by OH, oxo, CF₃, methoxy or ethoxy, and Q represents hydrogen; —NR₈R₈ wherein each R₈ may be the same or different and selected from hydrogen, methyl, ethyl n- or isopropyl or tert-butyl; a methyl, ethyl or benzyl ester; or an optionally substituted phenyl, phenoxy, cyclopentyl, cyclohexyl, furyl, thienyl, piperidyl, or piperazinyl group; and
R₇ represents H or $C_1$-$C_6$alkyl; or when taken together with the atom or atoms to which they are attached R₆ and R₇ form an optionally substituted monocyclic heterocyclic ring having 5, 6 or 7 ring atoms.

17. A compound as claimed in claim 15 wherein the radical R₄X— is in the 4-position of the phenyl ring.

18. A compound as claimed in claim 16 wherein X is a bond and $R_4$ is —C(=O)$NR_6R_7$ wherein $R_6$ represents a radical of formula —(Alk)$_m$-Q wherein m is 1 Alk is —$CH_2$—, —$CH_2CH_2$, —$CH_2CH_2CH_2$—, or —$CH_2CH(CH_3)CH_2$—, or a divalent cyclopropylene, cyclopentylene or cyclohexylene radical, optionally substituted by OH, oxo, $CF_3$, methoxy or ethoxy, and Q represents hydrogen and $R_7$ represents H or $C_1$-$C_6$alkyl; or when taken together with the atom or atoms to which they are attached $R_6$ and $R_7$ form a monocyclic heterocyclic ring having 5, 6 or 7 ring atoms.

19. A pharmaceutical or veterinary composition comprising a compound as claimed in claim 1 together with a pharmaceutically or veterinarily acceptable excipient or carrier.

* * * * *